United States Patent

Grantz

[11] Patent Number: 6,129,705
[45] Date of Patent: Oct. 10, 2000

[54] DRUG DELIVERY AND GENE THERAPY DELIVERY SYSTEM

[75] Inventor: Stephen Grantz, Pelham, N.H.

[73] Assignee: Medtronic AVE, Inc., Santa Rosa, Calif.

[21] Appl. No.: 09/163,245

[22] Filed: Sep. 30, 1998

Related U.S. Application Data

[60] Provisional application No. 60/060,630, Oct. 1, 1997.

[51] Int. Cl.[7] .................................................. A61M 29/00
[52] U.S. Cl. ............................. 604/96; 604/104; 604/265
[58] Field of Search ............................. 604/96, 104, 265, 604/53, 103.01, 103.2; 606/194; 428/402.2, 402.22, 402.24

[56] References Cited

U.S. PATENT DOCUMENTS

| | | |
|---|---|---|
| 4,186,745 | 2/1980 | Lewis et al. . |
| 5,092,841 | 3/1992 | Spears ........................................ 604/96 |
| 5,102,402 | 4/1992 | Dror et al. ................. 604/265 |
| 5,112,305 | 5/1992 | Barath et al. .............................. 604/96 |
| 5,199,951 | 4/1993 | Spears . |
| 5,397,307 | 3/1995 | Goodin . |
| 5,547,472 | 8/1996 | Onishi et al. . |
| 5,609,629 | 3/1997 | Fearnot et al. ............................. 604/53 |
| 5,628,785 | 5/1997 | Schwartz et al. ........................ 604/104 |
| 5,674,192 | 10/1997 | Sahatjian et al. . |
| 5,697,967 | 12/1997 | Dinh et al. ................................ 604/104 |
| 5,800,507 | 9/1998 | Schwartz ................................. 604/104 |
| 5,824,049 | 10/1998 | Ragheb et al. ............................ 604/53 |
| 5,873,904 | 2/1999 | Ragheb et al. ............................ 604/53 |

FOREIGN PATENT DOCUMENTS

| | | |
|---|---|---|
| 0 747 069 A2 | 12/1996 | European Pat. Off. . |
| WO 94/21320 | 9/1994 | WIPO . |
| WO 95/03083 | 2/1995 | WIPO . |
| WO 98/34564 | 8/1998 | WIPO . |
| WO 98/34669 | 8/1998 | WIPO . |

*Primary Examiner*—Wynn Wood Coggins
*Assistant Examiner*—Kevin C. Sirmons
*Attorney, Agent, or Firm*—Sterne, Kessler, Goldstein & Fox P.L.L.C.

[57] ABSTRACT

A drug or gene therapy solution delivery system including a balloon catheter having a balloon associated with a distal end of the catheter, the balloon having an exterior surface and comprising: a plurality of microencapsulated spheres containing a drug or gene therapy solution, the microencapsulated spheres being disposed about the exterior surface of the balloon so as to rupture upon application of a predetermined pressure to the balloon. In one embodiment, the microencapsulated spheres are encapsulated in a coating applied to the exterior surface of the balloon. In another embodiment, the microencapsulated spheres are extruded in the balloon. In yet another embodiment, the invention provides a drug or gene therapy solution delivery system including a stent, the stent comprising: a plurality of microencapsulated spheres containing a drug or gene therapy solution delivery solution, the microencapsulated spheres being disposed about the exterior surface of the stent so as to rupture upon radial expansion of the stent by a predetermined amount.

1 Claim, 2 Drawing Sheets

DRUG DELIVERY AND GENE THERAPY DELIVERY SYSTEM

This application is based upon Provisional Patent Application Ser. No. 60/060,630, filed on Oct. 1, 1997.

FIELD OF THE INVENTION

The present invention relates generally to drug or gene therapy delivery system, and more particularly, to a drug or gene therapy delivery system in which microencapsulated spheres are coated on the exterior of a balloon angioplasty device and configured to rupture upon application of a predetermined pressure to cause the medicament to be administered to a patient.

DESCRIPTION OF THE PRIOR ART

The use of balloon catheters to administer medicaments to a patient is well known in the art. However, current devices suffer a drawback in that drug/gene solutions contained in coatings must be placed in contact with the artery wall for a long period of time. In this connection, the balloon must be inflated for a long duration, which can occlude blood flow. The actual quantity of drug/gene solution transfer to the anatomy of the artery is still unknown. Some of the drug/gene solution is believed to be washed downstream by the blood flow.

Examples of such arrangements are disclosed in U.S. Pat. Nos. 4,186,745 ("the '745 Patent"), 5,397,307 ("the '307 Patent"), and 5,547,472 ("the '472 Patent") and 5,674,192 ("the '192 Patent"). The '745 Patent teaches a catheter having a micropore structure over a portion of the catheter which permits the controlled release of substances such as sterile water, antiseptics, antibiotics, enzymes, and the like. The substances are released by differential thermal expansion of the catheter caused by contact with the patient.

The '307 Patent discloses an intravascular material delivery dilation catheter having a pair of spaced inflatable balloons defining a drug delivery region therebetween. One of the balloons is contoured to define fluid comminication paths when inflated. The other balloon has four lobes which are separated by grooves, which in combination with the inner wall of a blood vessel form fluid communication paths. Upon inflation of both balloons in the blood vessel, a medicament is injected via a drug delivery region between the inflated balloons, and flows past the distal balloon at a selected rate.

The '472 Patent teaches a balloon catheter including a tube or balloon provided with a plurality of pores, and a stimulus-responsive polymer attached to the pores such that fluid transmission through the pores is controllable by a stimulus change, such as, for example, a change in pH, composition, and temperature. The catheter can administer a limited amount of medicament to a locally limited site only when necessary.

The '192 Patent discloses a catheter having an expandable portion with an exterior surface defined by a coating of a swellable hydrogel polymer. An aqueous solution of a drug to be delivered to the wall of a body lumen is incorporated into the hydrogel polymer. Compression of the coating against the lumen wall causes release of the drug when the expandable portion is expanded.

In view of the foregoing, there exists a need for a new type of drug/gene therapy delivery system in which a predetermined pressure applied to the balloon causes the drug/gene therapy solution to be administered to a specific treatment area in an artery wall of the patient. Thus, the therapeutic contents may be infused into the artery wall for a more effective administration. Consequently, it is no longer necessary to inflate the balloon for long periods of time to effectuate release of the solution.

SUMMARY OF THE INVENTION

In accordance with the present invention, it is an object thereof to provide a drug delivery and gene therapy delivery system in which microencapsulated spheres are coated on the exterior of a balloon angioplasty device and configured to rupture upon application of a predetermined pressure to cause the medicament to be administered to a patient.

It is another object of the present invention to provide a drug delivery and gene therapy delivery system by which medical personnel can perform standard clinical procedures to locate the balloon at the preferred site to administer the medicament.

It is yet another object of the present invention to provide a drug delivery and gene therapy delivery system in which a balloon catheter is utilized to advance a balloon disposed proximal to or at a distal end of the catheter to a desired site within an artery, and to then inflate the balloon to a predetermined pressure to initially cause the encapsulated microspheres become embedded in an artery wall and to thereafter rupture to release the medicament.

It is still another object of the present invention to provide a drug delivery and gene therapy delivery system which can be utilized in all applications for balloon-type catheters, including peripherals.

It is yet another object of the present invention to provide a drug delivery and gene therapy delivery system which can be utilized in all urological applications, but which is not limited to such applications.

It is still another object of the present invention to provide a drug delivery and gene therapy delivery system in accordance with the foregoing which can be configured for use with a stent in lieu of a balloon catheter.

In accordance with the above objects and additional objects that will become apparent hereinafter, the present invention provides, in a first embodiment, a drug or gene therapy solution delivery system including a balloon catheter having a balloon associated with a distal end of the catheter, the balloon having an exterior surface and comprising: a plurality of microencapsulated spheres containing a medicament, the microencapsulated spheres being disposed about the exterior surface of the balloon so as to rupture upon application of a predetermined pressure to the balloon.

The microencapsulated spheres are encapsulated in a coating applied to the exterior surface of the balloon, or the microencapsulated spheres are extruded in the balloon.

In another embodiment, the present invention provides a drug or gene therapy solution delivery system including a stent capable of radial expansion, the stent comprising: a plurality of microencapsulated spheres containing a medicament, the microencapsulated spheres being disposed about the exterior surface of the stent so as to rupture upon radial expansion of the stent by a predetermined amount. The microencapsulated spheres are encapsulated in a coating applied to the exterior surface of the stent.

The present invention also provides a method for administering a drug or gene therapy solution to a patient, comprising the steps of:

(a) advancing a balloon catheter having a balloon with a plurality of microencapsulated spheres containing a medicament into an artery of a patient to a desired administration site;

(b) inflating the balloon to a first predetermined pressure sufficient to cause the microencapsulated spheres to become embedded in the artery;

(c) further inflating the balloon to a second higher predetermined pressure sufficient to cause the microencapsulated spheres to rupture and release the medicament into the artery wall; and (d) thereafter withdrawing the balloon catheter from the artery.

In another embodiment, the present invention provides a method for administering a drug or gene therapy solution to a patient, comprising the steps of:

(a) advancing a stent coated with a plurality of microencapsulated spheres containing a medicament into an artery of a patient to a desired administration site;

(b) radially expanding the stent by a first predetermined amount sufficient to cause the microencapsulated spheres to become embedded in the artery; and (c) further expanding the stent by a second higher predetermined amount sufficient to cause the microencapsulated spheres to rupture and release the medicament into the artery wall.

In accordance with the above objects and additional objects that will become apparent hereinafter, the present invention will now be described with particular reference to the accompanying drawings.

DETAILED DESCRIPTION OF THE PREFERRED EMBODIMENTS

Figure 1:
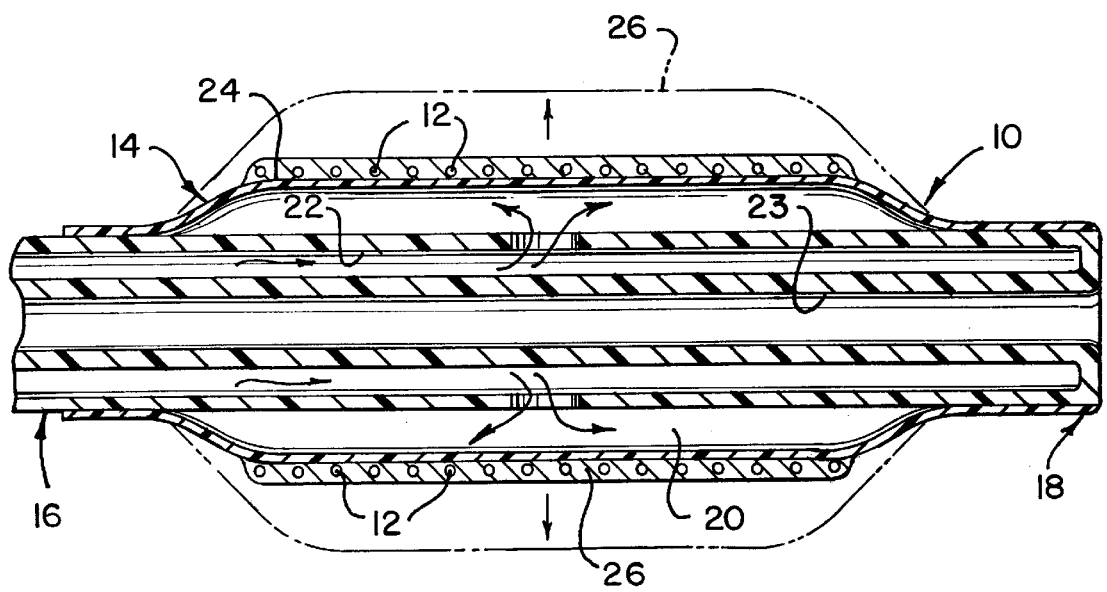
FIG. 1 is a sectional view of a balloon catheter and balloon in accordance with a first embodiment of the invention.

With reference to the several views of the drawings, the present invention provides a drug delivery and gene therapy delivery system 10 in one implementation in which microencapsulated spheres generally denoted by the reference numeral 12 are disposed on the exterior of or extruded within the wall of a balloon 14 associated with a balloon catheter 16. The balloon catheter 16 and balloon 14 are conventional and well known in the art. The balloon catheter 16 is surgically or percutaneously inserted into an artery of the patient. The balloon catheter 16 may be coupled to an external shuttle gas source (not shown) to inflate and deflate the balloon 14.

Figure 3:
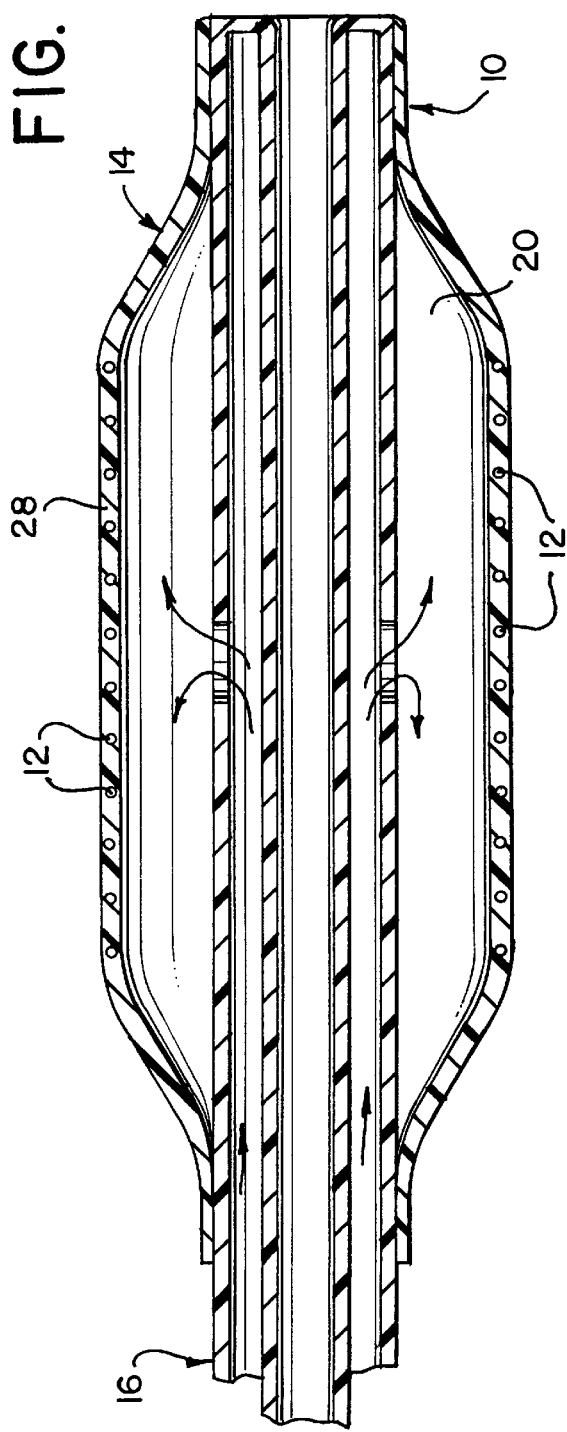
FIG. 3 is a sectional view of a balloon and balloon catheter having extruded microencapsulated spheres.
Figure 4:
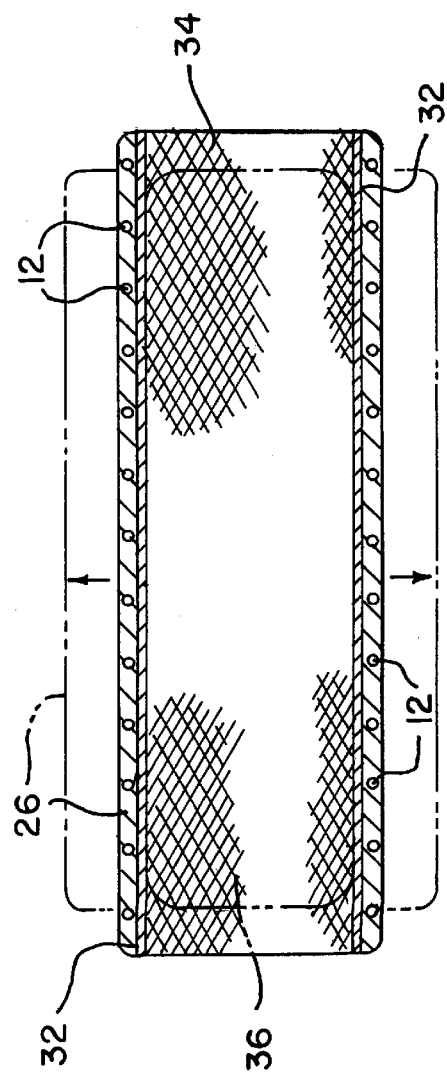
FIG. 4 is a sectional view of another embodiment in which a radially expandable stent is coated with a plurality of microencapsulated spheres.

Referring to FIG. 1, the balloon 14 is disposed proximal to or at the distal end 18 of the balloon catheter 16 in conventional fashion. The balloon 14 defines an interior chamber 20 communicating with a lumen 22 defined in the balloon catheter 16 to facilitate inflation and deflation thereof. The shuttle gas follows a flow passage from lumen 22 as shown by the arrows in FIG. 1. An inner lumen 23 is sized to permit a guidewire to pass therethrough. The balloon 14 includes an outer peripheral surface 24, on which a plurality of microencapsulated spheres 12 are impregnated in a coating material 26, which may be, but is not limited to, a hydrophilic material. The microencapsulated spheres 12 contain any available drugs or gene therapy solutions capable of breaking up clots, repairing or healing damaged arteries, and the like, and are immersed in the coating 26. In an alternative embodiment shown in FIG. 3, the microencapsulated spheres 12 are extruded in the wall 28 of the balloon during the manufacturing process. The microencapsulated spheres 12 are made from a biologically inert material, which may be a polymeric material, but is not limited to a polymeric material, and are sized (on the order of 5 $\mu$, but not limited to such size) and configured to rupture upon application of a predetermined pressure caused by inflating the balloon 14. The microencapsulated spheres 12 are fabricated with a quantity of medicament in accordance with known techniques. For example, these are described in articles entitled Intelligent Gels, Toyoichi Tanaka, Chemical & Engineering News, Page 26, Jun. 9, 1997, and Double Wall Microspheres—Advanced Drug Delivery, R & D, Page 64, March 1994. The technology described in the R & D Article has been licensed by Alkermes, of Cambridge Mass. The density of microencapsulated spheres 12 in the coating 26 is a function of the size of the spheres, balloon surface area and desired quantity of medicament to be administered. The coating typically comprises a hydrophilic material, although other materials may be employed within the scope of the invention, and is on the order of about 5 $\mu$in thickness, but is not limited to such size.

Figure 2:
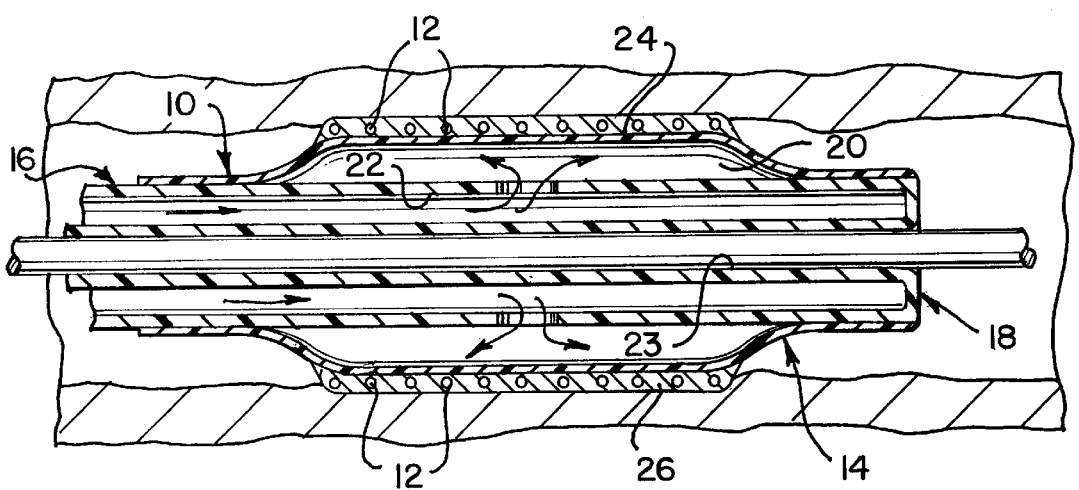
FIG. 2 is a sectional view of a balloon and balloon catheter inserted into an artery of the patient with the balloon inflated to cause the microencapsulated spheres to become embedded in the wall of the artery.

The present invention allows for the microspheres 12 to become embedded in an artery wall 30 when an initial pressure is communicated to the balloon 14 as depicted in FIG. 2, and to thereafter rupture upon further inflation of the balloon 14 to cause the medicament to be administered to the patient. The amount of pressure required is a function of the balloon geometry and material, as well as the configuration of the microencapsulated spheres 12. The arrangement allows for the delivery of the medicament to a specific area, without undesirable occlusion of blood flow or dilution of the medicament. It also reduces the amount of time required for the balloon 14 to remain inflated within the artery. The microencapsulated sphere contents are infused directly into the artery wall, and consequently the delivery is more effective.

In another embodiment, the microencapsulated spheres 12 are disposed in a coating 26 on the exterior surface 32 of a stent 34. The stent 34 is advanced into the patient using conventional techniques such as over a guiding catheter (not shown) with an advancing catheter or element. The exterior surface 32 of the stent 34 is coated with the microspheres 12 in accordance with the techniques described in the foregoing. The stent 34 includes a mechanism generally denoted at 36 for radially expanding the stent 34 to cause the microencapsulated spheres 12 to become embedded in the artery wall 30 and thereafter to rupture to release the drug or gene therapy solution in a manner analogous to the balloon embodiment described above.

The present invention further provides a method for administering a drug or gene therapy solution to a patient, comprising the steps of:

(a) advancing a balloon catheter 16 having a balloon 14 with a plurality of microencapsulated spheres 12 containing a drug or gene therapy solution into an artery of a patient to a desired administration site;

(b) inflating the balloon 14 to a first predetermined pressure sufficient to cause the microspheres 12 to become embedded in the artery;

(c) further inflating the balloon 14 to a second higher predetermined pressure sufficient to cause the microencapsulated spheres 12 to rupture and release the drug or gene therapy solution into the artery wall 30; and (d) thereafter withdrawing the balloon catheter 16 from the artery.

In another embodiment, there is also provided a method for administering a drug or gene therapy solution to a patient, comprising the steps of:

(a) advancing a stent 34 coated with a plurality of microspheres 12 containing a drug or gene therapy solution into an artery of a patient to a desired administration site;

(b) radially expanding the stent 34 by a first predetermined amount sufficient to cause the microencapsulated spheres 12 to become embedded in the artery; and (c) further expanding the stent 34 by a second higher predetermined amount sufficient to cause the microencapsulated spheres 12 to rupture and release the drug or gene therapy solution into the artery wall 30.

The present invention has been shown and described in what are considered to be the most practical and preferred embodiments. It is anticipated, however, that departures may be made therefrom and that obvious modifications will occur to persons skilled in the art.

What is claimed is:

1. A drug or gene therapy solution delivery system including a balloon catheter having a balloon associated with a distal end of said catheter, comprising:

a plurality of microencapsulated spheres containing a medicament formed into a wall of said balloon so as to rupture upon application of a predetermined pressure to said balloon wherein said microencapsulated spheres are extruded within said balloon wall.

* * * * *